United States Patent [19]

Frigerio et al.

[11] Patent Number: 4,935,433
[45] Date of Patent: Jun. 19, 1990

[54] 2-(ACYLTHIO)METHYL DIHYDROPYRIDINES, AND PHARMACEUTICAL COMPOSITIONS CONTAINING THEM

[75] Inventors: Marco Frigerio; Carlo Riva; Andrea Zaliani; Carmelo A. Gandolfi; Odoardo Tofanetti; Sergio Tognella, all of Milan, Italy

[73] Assignee: Boehringer Mannheim Italia, S.p.A., Milan, Italy

[21] Appl. No.: 80,397

[22] Filed: Jul. 28, 1987

[30] Foreign Application Priority Data

Jul. 29, 1986 [IT] Italy .................. 21290 A/86

[51] Int. Cl.$^5$ ............... C07D 211/86; A61K 31/455
[52] U.S. Cl. ............................ 514/356; 514/343; 514/255; 514/318; 514/227.8; 514/237.2; 546/321; 546/194; 546/281; 544/131; 544/58.4; 544/365
[58] Field of Search ............ 544/365, 333, 59.6, 544/131, 58.4; 546/270, 256, 278, 283, 284, 281, 286, 194, 310, 316, 318, 321, 322; 514/225, 236, 252, 256, 318, 333, 334, 338, 341, 336, 343, 344, 352, 356, 222, 255

[56] References Cited

U.S. PATENT DOCUMENTS

| 4,284,634 | 8/1981 | Sato ..................... | 514/344 |
| 4,404,378 | 9/1983 | Miyano et al. ......... | 546/321 |
| 4,492,703 | 1/1985 | Goldmann et al. .... | 546/321 |
| 4,532,248 | 7/1985 | Franckowiak et al. | 546/321 |
| 4,642,310 | 2/1987 | Goldmann et al. .... | 514/301 |

FOREIGN PATENT DOCUMENTS

| 101023 | 2/1984 | European Pat. Off. ....... | 546/321 |
| 152373 | 8/1984 | Japan . | |
| 00836 | 2/1987 | PCT Int'l Appl. ............ | 546/321 |

OTHER PUBLICATIONS

Merk Index 9th edition, pp. 7853-7854.

Primary Examiner—Jane T. Fan
Attorney, Agent, or Firm—Armstrong, Nikaido, Marmelstein, Kubovcik & Murray

[57] ABSTRACT

Compounds of formula I wherein $R_1$ is an alkoxy carbonyl, aminocarbonyl, acetyl, benzyl, cyano or nitro group; $R_2$ is as optionally substituted phenyl, aryl, hetaryl residue; $R_3$ is an alkoxy-carbonyl group, X is an oxygen or sulphur atom, $R_4$ is hydrogen, an optionally substituted alkyl, cycloalkyl, alkenyl group, Y is a single bond oxygen, sulphur or substituted nitrogen atom.

Compounds of formula I are prepared by acylation from a 2-mercaptomethyl-1,4-dihydropyridine and are useful in therapy.

6 Claims, No Drawings

2-(ACYLTHIO)METHYL DIHYDROPYRIDINES, AND PHARMACEUTICAL COMPOSITIONS CONTAINING THEM

The present invention relates to 2-(acylthio)-methyl-dihydropyridines, to a method for their preparation and to pharmaceutical compositions containing them.

The compounds of the invention have the following formula I

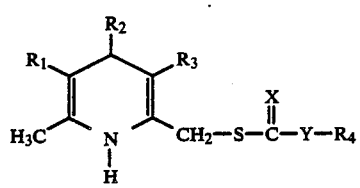

wherein $R_1$ is:

a $COCH_3$, $COC_6H_5$, CN or $NO_2$ group;

a $COOR_5$ group wherein $R_5$ is hydrogen; a cation of an alkaline metal or ammonium; linear or branched $C_1-C_6$ alkyl; hydroxy; primary, secondary, tertiary or cyclic aminogroups (the cycle may contain also other heteroatoms); $C_2-C_6$-alkenyl; optionally substituted phenyl; optionally substituted phenyl ($C_1-C_4$)alkyl;

a $CONR_6R_7$ group, wherein $R_6$ and $R_7$, which are the same or different, are hydrogen, $C_1-C_6$-alkyl, phenyl or benzyl;

$R_2$ is:

a phenyl residue substituted or unsubstituted with one or more halogen atoms, alkyl, haloalkyl, $C_1-C_4$-alkoxy or haloalkoxy groups, nitro, cyano; ($C_1-C_6$) alkoxycarbonyl; S-(-$C_1-C_6$)alkyl; SO-(-$C_1-C_6$)alkyl groups;

a pentafluorophenyl residue;

a α or β-naphthyl residue;

a 5- or 6-membered heteroaromatic residue, particularly pyridyl, furanyl or thienyl;

a residue of formula

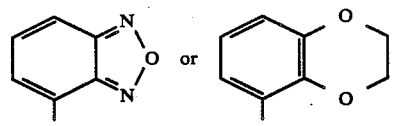

$R_3$ is a $COOR_5$ group wherein $R_5$ is as above defined;

$R_4$ is selected in the group consisting of:
hydrogen;
linear or branched $C_1-C_{20}$ alkyl;
$C_3-C_7$ cycloalkyl;
alkenyl $C_2-C_{10}$;
$C_1-C_{20}$ alkyl or alkenyl groups substituted by one or more $C_3-C_7$-cycloaklyl, hydroxy, $C_1-C_4$-alkoxy, $C_1-C_4$-alkylthio, $C_1-C_4$ acylthio, amino (N Ra Rb), $C_1-C_4$-acylamino groups, groups of formula $COOR_5$, phenoxy or optionally substituted phenyl with $C_1-C_3$-alkoxy, hydroxy or amino (N Ra Rb) groups;

phenyl optionally mono- or poly-substituted with halogen atoms, hydroxy, $C_1-C_3$-alkoxy, $C_1-C_3$ acyloxy, amino (N Ra Rb), $C_1-C_4$ acylamino, halogen (fluorine, chlorine, bromine or iodine), nitro, $C_1-C_3$-alkylthio groups;

heteroaryl selected in the group of imidazole, furan, thiophene, pyridine, pyrimidine optionally mono- or polysubstituted by halogen atoms, $C_1-C_3$ alkyl or $COOR_5$ carboalkoxy groups;

Ra and Rb, which are the same or different, are selected in the group of hydrogen, $C_1-C_4$ alkyl, phenyl, benzyl, or taken together with the nitrogen atom to which they are bound, form a piperidine, pyrrolidine, morpholine, thiomorpholine ring or a group of formula

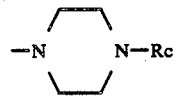

wherein Rc is $C_1-C_3$ alkyl, bis-phenylmethyl, bis (p-fluorophenyl)-methyl;

X is O or S (oxygen or sulphur);

Y is a single bond, O, S or N—Rd, wherein Rd is hydrogen, $C_1-C_4$-alkyl, benzyl or phenyl; moreover, when Y is NRd, Rd and $R_4$, taken together with the nitrogen atom to which they are bound, may form a piperidine, pyrrolidine, morpholine, thiomorpholine ring or a group

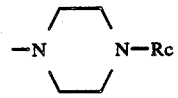

wherein Rc is as above defined, provided that when $R_4$ is $C_1-C_7$-alkyl, $R_1$ is different from $COOR_5$.

Pharmaceutically active salts, optical antipodes, i.e. the single enantiomers, and the racemic mixtures of compounds of formula I are also included in the scope of the present invention.

According to the invention, the alkyl, alkenyl, alkoxy, alkylthio, acyloxy, acylthio and acylamino groups may have both linear and branched chain.

Pharmaceutically acceptable salts of compounds I of the invention are those with pharmaceutically acceptable acids and bases.

Specific examples of compounds of the invention are listed in Table I.

TABLE I

| N° | $R_1$ | $R_2$ | $R_3$ | $R_4$ | X | Y |
|---|---|---|---|---|---|---|
| 1 | $COOC_2H_5$ | m-nitrophenyl | $COOC_2H_5$ | phenyl | O | — |
| 2 | $COOC_2H_5$ | m-nitrophenyl | $COOC_2H_5$ | p-$NH_2$-phenyl | O | — |
| 3 | $COOCH_3$ | m-nitrophenyl | $COOC_2H_5$ | phenyl | O | — |
| 4 | $COOC_2H_5$ | m-chlorophenyl | $COOC_2H_5$ | phenyl | O | — |
| 5 | $COOCH_3$ | m-trifluoro-methylphenyl | $CO_2C_2H_5$ | p-$NH_2$-phenyl | O | — |
| 6 | $COOC_2H_5$ | o-nitrophenyl-phenyl | $CO_2C_2H_5$ | p-$NH_2$-phenyl | O | — |
| 7 | $COOC_3H_7$-i | m-nitrophenyl | $COOC_2H_5$ | 3,4,5-trimethoxy-phenyl | O | — |
| 8 | $COOC_2H_5$ | m-nitrophenyl | $COOC_2H_5$ | 3,4,5-trimethoxy-phenyl | O | — |

TABLE I-continued

| N° | $R_1$ | $R_2$ | $R_3$ | $R_4$ | X | Y |
|---|---|---|---|---|---|---|
| 9 | $COOC_2H_5$ | m-nitrophenyl | $COOC_2H_5$ | 4-fluorophenyl | O | — |
| 10 | $COOC_2H_5$ | m-chlorophenyl | $COOC_2H_5$ | 4-fluorophenyl | O | — |
| 11 | $COOC_2H_5$ | o-methylthio-phenyl | $CO_2C_2H_5$ | 3-nitrophenyl | O | — |
| 12 | $COOC_2H_5$ | m-nitrophenyl | $COOC_2H_5$ | 3-nitrophenyl | O | — |
| 13 | $CO_2CH_2CH_2N(CH_3)-CH_2\phi$ | m-nitrophenyl | $COOC_2H_5$ | phenyl | O | — |
| 14 | $COOC_2H_5$ | o-chlorophenyl | $COOC_2H_5$ | —CH=CH-$\phi$ | O | — |
| 15 | $COOC_2H_5$ | m-nitrophenyl | $COOC_2H_5$ | —CH=CH-$\phi$ | O | — |
| 16 | $COOC_2H_5$ | m-nitrophenyl | $COOC_2H_5$ | $HC=CH-C_6H_4-pNH_2$ | O | — |
| 17 | $COOC_2H_5$ | m-nitrophenyl | $COOC_2H_5$ | p-OH-m-$OCH_3$-phenyl | O | — |
| 18 | $COOC_2H_5$ | m-nitrophenyl | $COOC_2H_5$ | 2-$OCH_3$-3-OH-5-(4-methylpiperazin-1-yl)phenyl | O | — |
| 19 | $COOCH_3$ | m-chlorophenyl | $COOCH_3$ | —HC=CH-(2-$OCH_3$-4-OH-phenyl) | O | — |
| 20 | $COOCH_3$ | m-nitrophenyl | $COOC_2H_5$ | -3-pyridyl | O | — |
| 21 | $COOC_2H_5$ | m-chlorophenyl | $COOC_2H_5$ | 3-pyridyl | O | — |
| 22 | $COOC_3H_7$-i | m-trifluoro-methyl-phenyl | $COOC_2H_5$ | 3-pyridyl | O | — |
| 23 | $COOC_2H_5$ | m-nitrophenyl | $COOC_2H_5$ | 5-bromopyrid-3-yl | O | — |
| 24 | $COOCH_3$ | m-nitrophenyl | $COOC_2H_5$ | 5-bromopyrid-3-yl | O | — |
| 25 | $COOCH_3$ | p-fluorophenyl | $COOC_2H_5$ | 5-bromopyrid-3-yl | O | — |
| 26 | $COOCH_3$ | m-nitrophenyl | $COOC_2H_5$ | 2-thienyl | O | — |
| 27 | $CONH_2$ | m-chlorophenyl | $COOC_2H_5$ | 2-furyl | O | — |
| 28 | $COOC_2H_5$ | m-nitrophenyl | $COOC_2H_5$ | phenyl | S | — |
| 29 | $COOCH_3$ | m-chlorophenyl | $COOC_2H_5$ | phenyl | S | — |
| 30 | $COOC_2H_5$ | m-trifluoro-methyl-phenyl | $COOC_2H_5$ | n-butyl | O | — |
| 31 | $COOC_3H_7$ | m-chlorophenyl | $COOC_2H_5$ | 3-acetaminopropyl | O | — |
| 32 | $COOC_2H_5$ | m-chlorophenyl | $COOC_2H_5$ | 2-cyclohexylethyl | O | — |
| 33 | $COOC_2H_5$ | m-nitrophenyl | $COOC_2H_5$ | 2-cyclohexylethyl | O | — |
| 34 | $COOC_2H_5$ | m-nitrophenyl | $COOC_2H_5$ | phenoxymethyl | O | — |
| 35 | $COOCH_3$ | m-chlorophenyl | $COOC_2H_5$ | acetylthiomethyl | O | — |
| 36 | $COOC_2H_5$ | m-nitrophenyl | $COOC_2H_5$ | acetylthiomethyl | O | — |
| 37 | $COOC_2H_5$ | m-nitrophenyl | $COOC_2H_5$ | $C_6H_5$—$CH_2$—CH($NH_2$)— | O | — |
| 38 | $COOCH_3$ | m-trifluoro-methylphenyl | $COOC_2H_5$ | — | O | N—$(C_2H_5)_2$ |
| 39 | $COOC_2H_5$ | m-nitrophenyl | $COOC_2H_5$ | — | O | N—$(C_2H_5)_2$ |
| 40 | $COOC_2H_5$ | m-nitrophenyl | $COOC_2H_5$ | 1-amino-2-phenylethyl | O | — |
| 41 | $COOCH_3$ | m-chlorophenyl | $COOC_2H_5$ | ethyl | O | O |
| 42 | $COOC_2H_5$ | m-nitrophenyl | $COOC_2H_5$ | ethyl | O | O |
| 43 | $COOC_2H_5$ | m-trifluoro-phenylethyl | $COOC_2H_5$ | benzyl | O | O |
| 44 | $COOC_2H_5$ | m-nitrophenyl | $COOC_2H_5$ | ethyl | S | O |
| 45 | $COOC_2H_5$ | m-nitrophenyl | $COOC_2H_5$ | 2-(piperid-1-yl)ethyl | O | O |
| 46 | $COOC_2H_5$ | m-chlorophenyl | $COOC_2H_5$ | 2-acetaminoethyl | O | O |
| 47 | $COOCH_3$ | p-fluorophenyl | $COOC_2H_5$ | phenyl | O | S |
| 48 | $COOC_2H_5$ | m-nitrophenyl | $COOC_2H_5$ | phenyl | S | S |
| 49 | $COCH_3$ | m-nitrophenyl | $COOC_2H_5$ | phenyl | O | — |
| 50 | $COC_6H_5$ | m-chlorophenyl | $COOC_2H_5$ | phenyl | O | — |
| 51 | $NO_2$ | m-trifluoro-methylphenyl | $COOC_2H_5$ | phenyl | O | — |
| 52 | $COOC_2H_5$ | m-nitrophenyl | $COOC_2H_5$ | 4-amino-2-hydroxyphenyl | O | — |
| 53 | $COOC_2H_5$ | m-nitrophenyl | $COOCH_3$ | 4-methylamino-2-hydroxyphenyl | O | — |
| 54 | $COOCH_3$ | m-chlorophenyl | $COOC_2H_5$ | 4-diethylamino-2-hydroxyphenyl | O | — |

TABLE I-continued

| N° | R₁ | R₂ | R₃ | R₄ | X | Y |
|---|---|---|---|---|---|---|
| 55 | COOC₂H₅ | m-trifluoro-methylphenyl | COOC₂H₅ | 4-amino-2-methoxy-phenyl | O | — |
| 56 | COOC₂H₅ | m-nitrophenyl | COOC₂H₅ | 4-butylamino-2-methoxyphenyl | O | — |
| 57 | COOCH₃ | p-fluorophenyl | COOC₂H₅ | 4-dimethylamino-2-ethoxyphenyl | O | — |

The compounds of the invention are prepared by a process comprising the reaction of a 2-mercaptomethyl-1,4-dihydropyridine of formula II

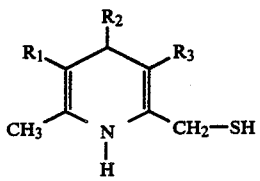

wherein $R_1$, $R_2$ and $R_3$ are as above defined, with a compound of formula III

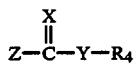

wherein $R_4$, X and Y are as above defined and Z is an activating group of the carboxylic group such as chlorine, bromine, 1-imidazolyl, azide, or an anhydride residue.

The obtained compounds of formula I may be then subjected to saponification, salification, esterification, amidation and/or optical resolution processes.

The acylation reaction of a 2-mercapto-methyl-1,4-dihydropyridine of formula II with a compound of formula III is carried out in an inert solvent, for instance an ether such as dimethoxyethane, dioxane, tetrahydrofuran; a chlorinated solvent, such as dichloromethane, chloroform, 1,2-dichloroethane; an amide, such as formamide, dimethylformamide, acetamide; an aromatic solvent, such as pyridine, 2 or 4-picoline or mixtures thereof, at temperatures ranging from −20° C. to the solvent's reflux temperature, but preferably from −10° C. to room temperature. The reaction time ranges from few minutes to 48 hours.

When the activating group Z is chlorine or bromine the presence of a base, such as triethylamine, dimethylbenzamine, N-methyl piperidine, pyridine, 4-dimethylpyridine, is usually required.

Activating groups Z (compounds of formula III) can be produced "in situ" by the corresponding acid of formula IV

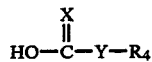

wherein $R_4$ and X are as above defined, and Y is preferably a single bond.

The resulting compounds III may be isolated or, more conveniently, directly used in solution for the acylation reaction of compounds II.

Compounds IV are then reacted in the above mentioned solvents with a reagent selected in the group of phosphonium oxychloride, phosphorus pentabromide, thionyl chloride, thionyl bromide, diphenylphosphorylchloride, diethoxyphosphorylchloride, diethoxyphosphorylazide, ethoxyphosphoryl chloride, dimethylaminophosphonyl dichloride, bis-(2-oxo-3-oxazolinyl)-phosphorylchloride, diethoxy-(2-oxo-3-oxazolinyl)-phosphorylamide, carbonyldiimidazole, dicycloexylcarbodiimide, to give compounds III.

Said reaction is carried out at temperatures ranging from −20° C. to the solvent's reflux temperature, but preferably from −10° C. to the room temperature, for periods ranging from few minutes to 4 hours.

The compounds of formula I wherein COOR₅ is a free carboxyl group, can be salified with pharmaceutically acceptable bases.

If optically active bases such as (+) and (−) ephedrine, (+) and (−) phenylethylamine, dehydrobiethylamine, cynconine, cynconidine are used, the obtained salts can be submitted to optical resolution, thus obtaining the single optical antipodes of compounds I.

Similarly, compounds I having basic groups may be salified with pharmaceutically acceptable acids. If said acids are optically active, such as tartaric, mandelic, malic, camphosulphonic acids, the corresponding salts can be subjected to optical resolution, to give the single optical antipodes of compounds I;

Compounds of formula II are disclosed in PCT/EP 86/00445. Compounds of formula III are known and/or commercially available or they may be prepared according to known methods, similarly to compounds IV.

Compounds of formula IV are also known and/or commercially available.

Alternatively, the compounds of the invention may be obtained by reacting a 2-halomethyl-1,4-dihydropyridine V

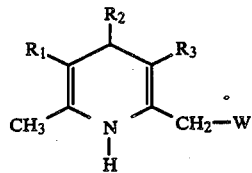

wherein $R_1$, $R_2$ and $R_3$ are as above defined and W is chlorine, bromine or iodine, with a thioacid of formula VI

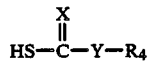

wherein $R_4$, X and Y are as above defined.

The reaction is carried out with a molar excess of an alkaline or alkaline-earth salt of compound VI in inert solvents, e.g. alcohols such as methanol, ethanol, isopropanol, n-butanol; ethers such as tetrahydrofuran, dioxane, dimethoxyethane; amides such as formamide, acetamide, dimethylacetamide; ketones such as acetone, methylethylketone or acetals such as methylal, or mixtures thereof, at temperatures ranging from −20° C. to the solvent's reflux temperature, but preferably from −15° C. to the room temperature, for a period from 2 to 48 hours.

Compounds of formula V are disclosed in EP-A-0212340.

Compounds of formula VI are known or prepared by known methods.

Alternatively, the compounds of the invention, of formula Ia

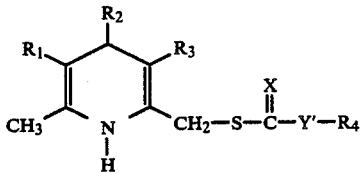

wherein $R_1$, $R_2$, $R_3$, $R_4$ and X are as above defined and Y' is O, S or N—Rd, may be prepared by reacting a 1,4-dihydropyridine of formula VII

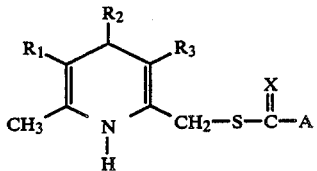

wherein $R_1$, $R_2$, $R_3$ and X are as above defined and A is chlorine or 1-imidazolyl, with a compound of general formula VIII $$R_4\text{—Y'—H} \qquad \text{VIII}$$

wherein $R_4$ and Y' are as above defined.

Reaction between a dihydropyridine VII and a compound VIII is carried out in a solvent such as tetrahydrofuran, dimethoxyethane, dioxane, dimethylformamide, dimethylacetamide, chloroform, methylene chloride or mixtures thereof at temperatures ranging from −30° C. to the solvent's reflux temperature, but preferably from −20° C. to room temperature, for a time ranging from few minutes to 4 hours.

Compounds VII are prepared from compounds II by reaction with equimolecular amounts of phosphene, thiophosphene, carbonylimidazole or thiocarbonylmidazole.

The reaction is carried out in an inert solvent such as tetrahydrofuran, dimethoxyethane, dioxane, dimethylformamide, dimethylacetamide, chloroform or methylene chloride at temperatures ranging from −30° C. to the solvent's reflux temperature, but preferably from −20° C. to 0° C., for reaction periods ranging from a few minutes to two hours.

Compounds of formula VIII are known and/or commercially available.

The compounds of the invention show an anti-hypertensive activity "in vivo" and a calcium-antagonist activity "in vitro".

They are therefore useful for treating diseases in cardiocirculatory system, such as angina and coronary pathologies.

Some of the compounds of the invention have also local anesthetic activity.

The present invention concerns also all the industrially applicable aspects connected with the therapeutic use of compounds of formula I. An essential characteristic of the invention is therefore provided by pharmaceutical compositions containing a compound I admixed with suitable pharmaceutical vehicle, in form of tablets, pills, powders, granules for oral solutions or suspensions, syrups, vials for parenteral administration, etc.

Active principles may also be administered in capsules. The pharmaceutical compositions may be prepared using well known techniques and the usual pharmaceutical vehicles, e.g. excipients such as lactose or talc, granulating agents such as magnesium stearate and stearic acid, suspending agents, such as methylcellulose and/or tensioactive agents such polyoxyethylstearate; preserving agents such as ethyl p-hydroxybenzoate, aromatic agents, etc.

The pharmaceutical compositions of the present invention are preferably formulated in unit doses containing from 1 to 500 mg of compound of formula I. Said unit doses may be administered once or more times per day.

The following examples describe but do not limit the invention.

EXAMPLE 1

A mixture of 2-mercaptomethyl-3,5-dicarboethoxy-4-m-nitrophenyl)-6-methyl-1,4-dihydropyridine (250 mg) m-nitrobenzoyl chloride (137 mg), triethylamine (0,130 ml), methylene chloride (3 ml) is stirred in nitrogen atmosphere at room temperature, for two hours.

The solvent is then evaporated in vacuum and the residue is dissolved in ethyl ester (20 ml), washed with water (2×20 ml), sodium bicarbonate solution (2×5 ml) and once again with water (2×20 ml). After drying on sodium sulphate, the products is purified by elution (ethyl ether/ethyl acetate 85/15) on silica gel.

280 mg of 2-[(m-nitrobenzoyl)thio]methyl-3,5-dicarboethoxy-4-(m-nitrophenyl)-6-methyl-1,4-dihydropyridine are obtained as an oil.

NMR (CDCl$_3$) (TMS)=1.10–1.40 (6H, t), 2.40 (3H, s), 3.90–4.40 (4H, q), 4.50 (2H, s), 5.16 (1H, s), 7.15–8.80 (9H, m).

According to the above conditions and using a 2-mercaptomethyl-1,4-dihydropyridine selected in the group of 2-mercaptomethyl-3-carboethoxy-5-carbomethoxy-4-(m-nitrophenyl)-6-methyl-1,4-dihydropyridine, 2-mercaptomethyl-3,5-dicarboethoxy-4-(m-nitrophenyl)-6-methyl-1,4-dihydropyridine and 2-mercaptomethyl-3,5-dicarboethoxy-4-(m-chlorophenyl)-6-methyl-1,4-dihydropyridine and an acyl chloride selected in the group of benzoylchloride, p-fluorobenzoylchloride, phenoxyacetylchloride, acetylthioacetylchloride, 2,4,5-trimethoxybenzoylchloride and ethyl chloroformate in methylene chloride or 1,2-dichloroethane, the following products were obtained:

-2-[(p-fluorobenzoyl)thio]methyl-3,5-dicarboethoxy-4-(m-nitrophenyl)-6-methyl-1,4-dihydropyridine, oil:
NMR (δ, CDCl$_3$) 1.00–1.40 (6H, t), 2.32 (3H, s), 3.85–4.30 (4H, q), 4.40 (2H, s), 5.10 (1H, s), 7.02–8.12 (9H, m).

-2-(benzoylthio)methyl-3,5-dicarboethoxy-4-(m-chlorophenyl)-6-methyl-1,4-dihydropyridine, oil:
NMR (δ, CDCl$_3$) 1.05–1.38 (6H, t), 2.30 (3H, s), 3.80–4.20 (4H, q), 4.30 (2H, s), 5.10 (1H, s), 7.00–8.20 (10H, m).

-2-[(acylthioacetyl)thio]methyl-3,5-dicarboethoxy-4-(m-nitrophenyl)-6-methyl-1,4-dihydropyridine; m.p. 100°–102° C., -2-[(phenoxyacetyl)thio]methyl-3,5-dicarboethoxy-4-(m-nitrophenyl)-6-methyl-1,4-dihydropyridine; m.p. 129°-131° C., -2-[(3,4,5-trimethoxybenzoyl)thio]methyl-3,5-dicarboethoxy-4-(m-nitrophenyl)-6-methyl-1,4-dihydropyridine; m.p. 147°-149° C., -2-[(3,4,5-trimethoxybenzoyl)thio]methyl-3-carboethoxy-5-carbomethoxy-4-(m-nitrophenyl)-6-methyl-1,4-dihydropyridine; m.p. 130°-132° C., -2-[(3,4,5-trimethoxybenzoyl)thio]methyl-3,5-dicarboethoxy-4-(m-chlorophenyl)-6-methyl-1,4-dihydropyridine; m.p. 145°-148° C., -2-[(ethoxycarbonyl)thio]methyl-3,5-dicarboethoxy-4-(m-nitrophenyl)-6-methyl-1,4-dihydropyridine; m.p. 111°-113° C., -2-[(ethoxycarbonyl)thio]methyl-3,5-dicarboethoxy-4-(m)chlorophenyl)-6-methyl-1,4-dihydropyridine; m.p. 95°-98° C.

EXAMPLE 2

A solution of cyclohexylpropionic acid (0.130 ml), triethylamine (0.103 ml) and phosphorus oxychloride (0.078 ml) in methylene chloride (8 ml) is stirred under nitrogen atmosphere, at 0° C. for 15 minutes, then it is warmed to room temperature for 15 minutes. A solution of 2-mercaptomethyl-3,5-dicarboethoxy-4-(m-nitrophenyl)-6-methyl-1,4-dihydropyridine (250 mg) and triethylamine (0.257 ml) in methylene chloride (3 ml) is dropped in the above solution. After 1 h the solvent is evaporated in vacuum, the residue is dissolved in ethyl acetate (20 ml), the organic phase is washed with water (2×20 ml), with a sodium bicarbonate solution (2×50 ml) and then with water (2×20 ml). The organic phase is dried on sodium sulphate, evaporated in vacuum and the residue is purified by chromatography on silica gel (g 6) eluting with ethyl ether/hexane (1/1). The product is then crystallized from ethyl ether.

220 mg of 2-[(3-cyclohexylpropionyl)thio]methyl-3,5-dicarboethoxy-4-(m-nitrophenyl)-6-methyl-1,4-dihydropyridine are obtained, m.p. 109°-112° C.

Operating in the preceding conditions and using a 2-mercaptomethyl-1,4-dihydropyridine selected in the group of 2-mercaptomethyl-3,5-dicarboethoxy-4-(m-nitrophenyl)-6-methyl-1,4-dihydropyridine, 2-mercaptomethyl-3-carboethoxy-5-carboisopropoxy-4-(m-trifluoromethylphenyl)-6-methyl-1,4-dihydropyridine and an acid selected in the group of nicotinic, p-amino-cinnamic, cinnamic, 2-thiophencarboxylic, stearic, 3-bromo-nicotinic acids, and using as activating agent a phosphorus derivative such as phosphorus oxychloride, diphenylphosphorylchloride, diethoxyphosphorylchloride, diethoxyphorylazide, ethoxyphosphoryldichloride, dimethylaminophosphorylchloride, bis-(2-oxo-3-oxazolidinyl)phosphoryl chloride, diethoxy-(2-oxo-3-oxazolidinyl)phosphoryl chloride, diethoxy-(2-oxo-3-oxazolinyl)-phosphorylamide, the following products were obtained:

-2-(nicotinoylthio)methyl-3,5-carboethoxy-4-(m-nitrophenyl)-6-methyl-1,4-dihydropyridine, oil
 NMR (δCDCl₃) 1.00-1.40 (6H, t), 2.32 (3H, s), 3.82-4.37 (4H, q), 4.48 (2H, s), 5.10 (1H, s), 7.10-9.30 (9H, m).

-2-(nicotinoylthio)methyl-3-carboethoxy-5-carboisopropoxy-4-(m-trifluoromethylphenyl)6-methyl-1,4-dihydropyridine, oil
 NMR (δCDCl₃) 1.01-1.45 (6H, t), 2.32 (3H, s), 3.85-4.40 (4H, q), 4.42 (2H, s), 5.17 (1H, s), 7.00-9.35 (9H, m).

-2-(5-bromonicotinoylthio)methyl-3-carboethoxy-5-carbomethoxy-4-(p-fluorophenyl)-6-methyl-1,4-dihydropyridine oil
 NMR (δCDCl₃) 1.01-1.45 (6H, t), 2.32 (3H, s), 3.85-4.40 (4H, q), 4.42 (2H, s), 5.17 (1H, s), 7.00-9.35 (9H, m).

-2-(5-bromonicotinoylthio)methyl-3-carboethoxy-5-carbomethoxy-4-(p-fluorophenyl)-6-methyl-1,4-dihydropyridine, oil -2-(5-bromonicotinoylthio)methyl-3,5-dicarboethoxy-4-(m-nitrophenyl)-6-methyl-1,4-dihydropyridine, oil -2-(cynnamoylthio)methyl-3,5-dicarboethoxy-4-(m-nitrophenyl)-6-methyl-1,4-dihydropyridine, m.p. 119°-120° C.

-2-(p-cinnamoylthio)methyl-3,5-dicarboethoxy-4-(m-nitrophenyl)-6-methyl-1,4-dihydropyridine, oil -2-[(thiophen-2-yl)-carbonylthio]methyl-3,5-dicarboethoxy-4-(m-nitrophenyl)-6-methyl-1,4-dihydropyridine, oil
 NMR (δCDCl₃) 1.07-1.42 (6H, t), 2.32 (3H, s), 3.95-4.38 (4H, q), 4.42 (2H, s), 5.10 (1H, s), 7.02-8.12 (8H, m).

-2-[(thiophen-2-yl)carbonylthio]methyl-3-carboethoxy-5-carboisopropoxy-4-(m-trifluoromethylphenyl)-6-methyl-1,4-dihydropyridine, oil -2-(stearoylthio)methyl-3,5-dicarboethoxy-4-(m-nitrophenyl)-6-methyl-1,4-dihydropyridine, oil
 NMR (δCDCl₃) 0.66-1.87 (41H, m), 2.30 (3H, s), 3.86-4.30 (6H, m), 5.05 (1H, s), 7.02-8.20 (5H, m).

EXAMPLE 3

A solution of dicyclohexylcarbodiimide (g 1.5) in tetrahydrofuran is added dropwise to a solution of 2-mercaptomethyl-3,5-dicarboethoxy-4-(m-nitrophenyl)-6-methyl-1,4-dihydropyridine (g 2.7) and p-aminobenzoic acid (g 1.0) in tetrahydrofuran (20 ml) cooled to 0° C. in nitrogen atmosphere, the mixture is stirred at 0° C. for 15 minutes and then warmed to room temperature for 18 hours. The precipitate formed is filtered and the solvent is evaporated in vacuum. The residue is dissolved in ethyl acetate (150 ml) and washed with water (3×40 ml), with a sodium bicarbonate solution (3×30 ml) and then once again with water (3×20 ml). After drying on sodium sulphate and evaporation in vacuum of the solvent, the residue is purified by chromatography on silica gel (g 100) eluting with petroleum ether-/ethyl acetate (8/2). The product is recrystallized from isopropyl ether. 3,2 g of 2-(p-aminobenzoylthio)methyl-3,5-dicarboethoxy-4-(m-nitrophenyl)-6-methyl-1,4-dihydropyridine are obtained; m.p. 78°-80° C.

Operating in the same conditions and using a 2-mercaptomethyl-1,4-dihydropyridine selected in the group of 2-mercaptomethyl-3-carboethoxy-5-carboethoxy-4-(m-trifluoromethylphenyl)-6-methyl-1,4-dihydropyridine and 2-mercaptomethyl-3,5-dicarboethoxy-4-(m-nitrophenyl)-6-methyl-1,4-dihydropyridine and p-aminobenzoic acid or N-(terbutoxycarbonyl)-phenylalanine, the following compounds were obtained:

-2-(p-aminobenzoyl)methyl-3-carboethoxy-5-carbomethoxy-4-(m-trifluoromethylphenyl)-6-methyl-1,4-dihydropyridine;

-2-[(3-phenyl-2-(N-terbutoxycarbonyl)aminopropionyl)thio]methyl-3,5-dicarboethoxy-4-(m-nitrophenyl)6-methyl-1,4-dihydropyridine, oil.

EXAMPLE 4

Trifluoroacetic acid (0.5 ml) is dropped in a solution of 2-[(3-phenyl-2-(N-terbutoxy-carbonyl)aminopropionyl)thio]methyl-3,5-dicarboethoxy-4-(m-nitrophenyl)-6-methyl-1,4-dihydropyridine (100 mg) in methylene chloride (0.5 ml), at 0° C.

After 30 minutes the organic solvent is evaporated in vacuum and the residue (20 ml) is then washed with ice-water (2×20 ml), with a saturated sodium bicarbonate solution at 5° C. (3×10 ml) and again with ice-water (3×10 ml). After drying on sodium sulphate, a drop of acetic acid (about 0.01 ml) is added before evaporating the solvent in vacuum, at a temperature lower than 40° C.

80 mg of 2-[(3-phenyl-2-aminopropionyl)thio]methyl-3,5-dicarboethoxy-4-(m-nitrophenyl)-6-methyl-1,4-dihydropyridine are obtained as an oil.

EXAMPLE 5

Carbon disulphide (0.390 ml), and after 15 minutes, a solution of 2-chloromethyl-3,5-dicarboethoxy-4-(m-nitrophenyl)-6-methyl-1,4-dihydropyridine (g 2.6) in ethanol (30 ml) are added dropwise to a solution of sodium ethylate, prepared "in situ" from sodium metal (147 mg), in ethanol (10 ml), under nitrogen atmosphere at a temperature of 0° C.

The solution is warmed to room temperature for 30 minutes, then for further 30 minutes to 50° C.

The solvent is evaporated in vacuum and the residue is dissolved in ethyl acetate (200 ml), washed with a monobasic sodium phosphate solution (2×30 ml) and water (3×50 ml), dried on sodium sulphate and concentrated in vacuum; the residue is crystallized from isopropyl ether 2.6 g of 2-[(ethoxythiocarbonyl)-thio]-methyl-3,5-dicarboethoxy-4-(m-nitrophenyl)-6-methyl-1,4-dihydropyridine are obtained; m.p. 119°-120° C.

EXAMPLE 6

2-(N-pyridinyl)-ethanol (0.88 ml) in tetrahydrofuran (9 ml) is dropped into a suspension of 80% sodium hydride (200 mg) in tetrahydrofuran (3 ml) under nitrogen atmosphere at −5° C. and then, when hydrogen evolution is over, carbon disulphide (0,41 ml).

After 15 minutes, a solution of 2-chloromethyl-3,5-dicarboethoxy-4-(m-nitrophenyl)-6-methyl-1,4-dihydropyridine (2.6 g) in tetrahydrofuran (2.6 ml) is added thereto.

The mixture is left for 30 minutes at −5° C., then at 50° C. for 40 minutes, finally cooled to room temperature, neutralized with a monobasic sodium phosphate solution, diluted with water (250 ml), extracted with ethyl acetate (5×50 ml), washed with water (2×30 ml), dried and evaporated.

The residue is purified by chromatography on silica gel (120 g) eluting with hexane/ethyl acetate (65/35) 2.2 g of 2-[(2-piperidin-1-yl)ethoxythiocarbonyl)thio]methyl-3,5-dicarboethoxy-4-(m-nitrophenyl)-6-methyl-1,4-dihydropyridine are obtained as an oil.

EXAMPLE 7

A solution of 2-mercaptomethyl-3,5-dicarboethoxy-4-(m-nitrophenyl)-6-methyl-1,4-dihydropyridine (270 mg) in tetrahydrofuran (3 ml) is added at 0° C. to a solution of carbonyldiimidazole (162 mg) in tetrahydrofuran (3 ml). After 15 minutes, the mixture is heated to room temperature and the solvent is evaporated in vacuum. The reaction product is directly purified by chromatography on silica gel (10 g) eluting with hexane/ethyl acetate (60/40).

200 mg of 2-[(imidazol-1-1)carbonylthio]methyl-3,5-dicarboethoxy-4-(m)nitrophenyl)-6-methyl-1,4-dihydropyridine are obtained as an oil.

We claim:

1. A compound of formula I

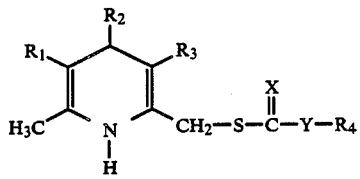

wherein $R_1$ is:
a $COOR_5$ group wherein $R_5$ is a linear or branched $C_1$-$C_6$ alkyl or $C_2$-$C_6$-alkenyl;
$R_2$ is selected from the group consisting of m-nitrophenyl, o-nitrophenyl, o-chlorophenyl, m-chlorophenyl, o-trifluoromethylphenyl, p-fluorophenyl and m-trifluoromethylphenyl
$R_3$ is a $COOR_5$ group wherein $R_5$ is as above defined;
$R_4$ is selected from the group consisting of:
linear or branched $C_1$-$C_6$ alkyl;
$C_2$-$C_6$ alkenyl;
$C_1$-$C_6$ alkyl substituted by amino (N Ra Rb);
phenyl optionally mono- or poly-substituted with hydroxy, $C_1$-$C_3$-alkoxy, $C_2$-$C_3$ acyloxy, amino (N Ra Rb), $C_2$-$C_4$ acylamino, a halogen selected from the group consisting of fluorine, chlorine, bromine and iodine, nitro, $C_1$-$C_3$-alkylthio groups;
Ra and Rb, which are the same or different, are selected from the group consisting of hydrogen, $C_1$-$C_4$ alkyl, phenyl, benzyl, or taken together with the nitrogen atom to which they are bound, form a piperidine, pyrrolidine, morpholine, thiomorpholine ring or a group of formula

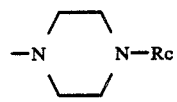

wherein Rc is $C_1$-$C_3$ alkyl, bis-phenylmethyl, bis (p-fluorophenyl)-methyl;
X is sulphur;
Y is a single bond, O or S, provided that when Y is a single bond, $R_4$ is not $C_1$-$C_6$ alkenyl, a pharmaceutically acceptable salt, enantiomer, diastereoisomer, or mixture of enantiomers or diastereoisomers thereof.

2. A compound according to claim 1 wherein Y is a single bond.

3. A compound according to claim 1 wherein Y is an oxygen or sulphur atom.

4. A compound according to any one of the preceding claims wherein $R_1$ and $R_3$, which may be the same or different, are methoxycarbonyl or ethoxycarbonyl.

5. A composition for therapy of hypertension comprising a therapeutically effective amount of the compound of claim 1 and a pharmaceutically acceptable carrier.

6. A method for treating hypertension, comprising administering a therapeutically effective amount of the compound of claim 1 to a patient.

* * * * *